US006458778B1

(12) United States Patent
Kong et al.

(10) Patent No.: US 6,458,778 B1
(45) Date of Patent: Oct. 1, 2002

(54) ESTRADIENES

(75) Inventors: Fangming Kong, Westwood, NJ (US); Leonard A. McDonald, Mountainside, NJ (US); Michael Z. Kagan, Plainsboro, NJ (US); Syed M. Shah, East Hanover, NJ (US); Panolil Raveendranath, Monroe, NY (US); Mark A. Collins, Norristown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/049,485

(22) Filed: Mar. 27, 1998

Related U.S. Application Data

(60) Provisional application No. 60/043,486, filed on Apr. 7, 1997, and provisional application No. 60/045,423, filed on May 2, 1997.

(51) Int. Cl.[7] ............................. A61K 31/56; C07J 1/00
(52) U.S. Cl. ....................... 514/178; 552/644
(58) Field of Search ........................ 514/178; 552/644

(56) References Cited

U.S. PATENT DOCUMENTS

| | | | |
|---|---|---|---|
| 2,834,712 A | | 5/1958 | Beall et al. |
| 2,930,805 A | | 3/1960 | Marshall et al. |
| 3,340,278 A | | 9/1967 | Kruger |
| 3,386,890 A | | 6/1968 | Vezina et al. |
| 3,407,190 A | | 10/1968 | Honjo et al. |
| 3,445,487 A | | 5/1969 | Phillipps |
| 3,450,697 A | | 6/1969 | Gale et al. |
| 3,608,077 A | * | 9/1971 | Ginsig .................. 424/243 |
| 3,644,439 A | | 2/1972 | Phillipps |
| 4,154,820 A | | 5/1979 | Simoons |
| 5,521,200 A | * | 5/1996 | Ho et al. .................. 514/338 |
| 5,652,228 A | * | 7/1997 | Bissett .................. 514/77 |
| 5,849,728 A | * | 12/1998 | Bissett .................. 514/159 |

FOREIGN PATENT DOCUMENTS

| | | |
|---|---|---|
| DE | 1093360 | 11/1960 |

OTHER PUBLICATIONS

Physicians' Desk Reference, 48th edition, pp. 2594–2596, 1994.*
Goodman and Gilman, 7th edition, pp. 1420–1423, 1985, 1994.*
Junghans, K. et al., Chem. Ber., Solvent effects in the electrochemical reduction of steroids with aromatic A and B rings, vol. 112, pp. 2631–2639, 1979.*
Database WPI, Section Ch, Derwent Publication Ltd., Class B01, AN 71–77128s (abstract of JP 46 040 939 B), 1968.
Chemical Abstracts, 76(7), No. 034484 (abstract of JP 46 040 939), 1968.
Junghans, K. et al., Chem. Ber., Solvent Effects in the Electrochemical Reduction of Steroids wit Aromatic A and B Rings, 112, 2631–2639 (1979).

* cited by examiner

*Primary Examiner*—Barbara P. Badio
(74) *Attorney, Agent, or Firm*—Arnold S. Milowsky

(57) ABSTRACT

This invention provides estra-5(10),7-dien-3β-ol-17-one or a pharmaceutically acceptable salt of its 3-sulfate ester, estra-5(10),7-dien-3β-ol-17-one 3-glucuronide or a pharmaceutically acceptable salt thereof, estra-5(10),7-dien-3α-ol-17-one or a pharmaceutically acceptable salt of its 3-sulfate ester, estra-5(10),7-dien-3β-ol-17-one 3-glucuronide or a pharmaceutically acceptable salt thereof, estra-5(10),7-dien-3β-ol-17-one 3-alkali metal salt, and estra-5(10),7-dien-3α-ol-17-one 3-alkali metal salt which are useful as estrogenic agents.

9 Claims, No Drawings

ESTRADIENES

This application claims the benefit of U.S. Provisional Application No. 60/043,486, filed Apr. 7, 1997 and No. 60/045,423, filed May 2, 1997.

BACKGROUND OF THE INVENTION

The use of naturally occurring estrogenic compositions of substantial purity and low toxicity such as PREMARIN (conjugated equine estrogens) has become a preferred medical treatment for alleviating the symptoms of menopausal syndrome, osteoporosis/osteopenia in estrogen deficient women and in other hormone related disorders. The estrogenic components of the naturally occurring estrogenic compositions have been generally identified as sulfate esters of estrone, equilin, equilenin, 17β-estradiol, dihydroequilenin and 17β-dihydroequilenin (U.S. Pat. No. 2,834,712). The estrogenic compositions are usually buffered or stabilized with alkali metal salts of organic or inorganic acids at a substantially neutral pH of about 6.5 to 7.5. Urea has also been used as a stabilizer (U.S. Pat. No. 3,608,077). The incorporation of antioxidants to stabilize synthetic conjugated estrogens and the failure of pH control with tris (hydroxymethyl)aminomethane (TRIS) to prevent hydrolysis is discussed in U.S. Pat. No. 4,154,820.

One of the compounds described herein, estra-5(10),7-dien-3β-ol-17-one 3-sulfate ester sodium salt is a minor component of PREMARIN (conjugated equine estrogens). The preparation of estra-5(10),7-dien-3β-ol-17-one and estra-5(10),7-dien-3α-ol-17-one have been disclosed by K. Junghans in Chem Ber. 112: 26 (1979); however, no utility is provided for this compound. U.S. Pat. No. 2,930,805 discloses the preparation of 3,17β-dihydroxy-5(10),7-estradienes, and their use as antiestrogens. U.S. Pat. No. 3,340,278 discloses the preparation of 5(10),7-estradien-3, 17-dione, 3,17β-dihydroxy-5(10),7-estradiene, and 17β-hydroxy -5(10),7-estradien-3-one, which are useful as intermediates in the preparation of equilin.

DESCRIPTION OF THE INVENTION

In accordance with this invention, there are provided estra-5(10),7-dien-3β-ol-17-one or a pharmaceutically acceptable salt of its 3-sulfate ester, estra-5(10),7-dien-3β-ol-17-one 3-glucuronide or a pharmaceutically acceptable salt thereof, estra-5(10),7-dien-3α-ol-17-one or a pharmaceutically acceptable salt of its 3-sulfate ester, and estra-5 (10),7-dien-3α-ol-17-one 3-glucuronide or a pharmaceutically acceptable salt thereof. This invention also provides a compound which is a 3-alkali metal salt of estra-5(10),7-dien-3β-ol-17-one or estra-5(10),7-dien-3α-ol-17-one. These are all collectively referred to as the compounds of this invention. The structures of estra-5(10),7-dien-3β-ol-17-one and estra-5(10),7-dien-3α-ol-17-one are shown below as compounds 5B and 5A, respectively.

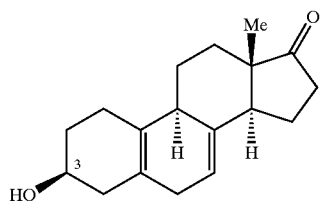

5B

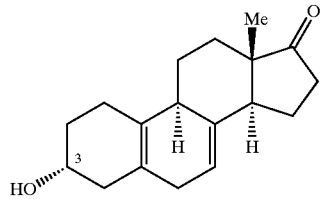

5A

Pharmaceutically acceptable salts of estra-5(10),7-dien-3β-ol-17-one 3-sulfate ester, estra-5(10),7-dien-3β-ol-17-one 3-glucuronide, estra-5(10),7-dien-3α-ol-17-one 3-sulfate ester, or estra-5(10),7-dien-3α-ol-17-one 3-glucuronide include, but are not limited to, the alkali metal salts, alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group. The alkali metal of the 3-alkali metal salts of estra-5(10),7-dien-3β-ol-17-one or estra-5 (10),7-dien-3α-ol-17-one are lithium, sodium, or potassium.

As estra-5(10),7-dien-3β-ol-17-one 3-sulfate ester sodium salt is a minor component of PREMARIN (conjugated equine estrogens), this invention also provides estra-5(10),7-dien-3β-ol-17-one 3-sulfate sodium salt in greater than one percent purity.

This invention also provides a compound consisting essentially of estra-5(10),7-dien-3β-ol-17-one or a pharmaceutically acceptable salt of its 3-sulfate ester or estra-5(10), 7-dien-3β-ol-17-one 3-glucuronide or a pharmaceutically acceptable salt thereof; and a compound consisting essentially of estra-5(10),7-dien-3α-ol-17-one or a pharmaceutically acceptable salt of its 3-sulfate ester or estra-5(10),7-dien-3α-ol-17-one 3-glucuronide or a pharmaceutically acceptable salt thereof.

As used in accordance with this invention, treating covers treatment of an existing condition, ameliorating the condition, or providing palliation of the condition and inhibiting includes inhibiting or preventing the progress or development of the condition.

The compounds of this invention can be prepared from readily available starting materials. For example, the preparation of estra-5(10),7-dien-3β-ol-17-one (5B), estra-5(10), 7-dien-3α-ol-17-one (5A), estra-5(10),7-dien-3α-ol-17-one 3-sulfate ester sodium salt (7), and estra-5(10),7-dien-3β-ol-17-one 3-sulfate ester triethylammonium salt (15) are shown in Schemes I and II starting from equilin methyl ether (U.S. Pat. No. 3,644,439, which is hereby incorporated by reference) and 17β-hydroxyestra-5(10),7-dien-3-one (8) (U.S. Pat. No. 2,930,805, which is hereby incorporated by reference). Estra-5(10),7-dien-3β-ol-17-one 3-glucuronide sodium salt (16) and estra-5(10),7-dien-3α-ol-17-one 3-glucuronide sodium salt (17) can be prepared according to Scheme III.

As shown in Scheme I, the 17-ethylenedioxy derivative of equilin methylether 1 is converted to the triene 2 utilizing a Birch reduction with lithium in liquid ammonia. Mild oxalic acid treatment allows the selective hydrolysis of the enol ether to provide the ketone 3. Sequential reduction of the 3-ketone (lithium aluminum hydride); and deprotection of the 17-ketone (p-tolunesulfonic acid) affords the products 5A and 5B of the invention as a mixture in which the 3α-isomer 5A predominates (4:1 ratio). Separation can be realized directly by preparative high pressure liquid chromatography. Alternatively, inversion of configuration at C-3 to a mixture in which the 3β-isomer predominates can be achieved by a Mitsunobu reaction. The highly crystalline 3-(3,5-dinitro)benzoates, products of the Mitsunobu inversion, are readily separable by column chromatography. After hydrolysis, 5B was converted to its 3,β-sulfate 7 with triethylamine:sufur trioxide reagent.

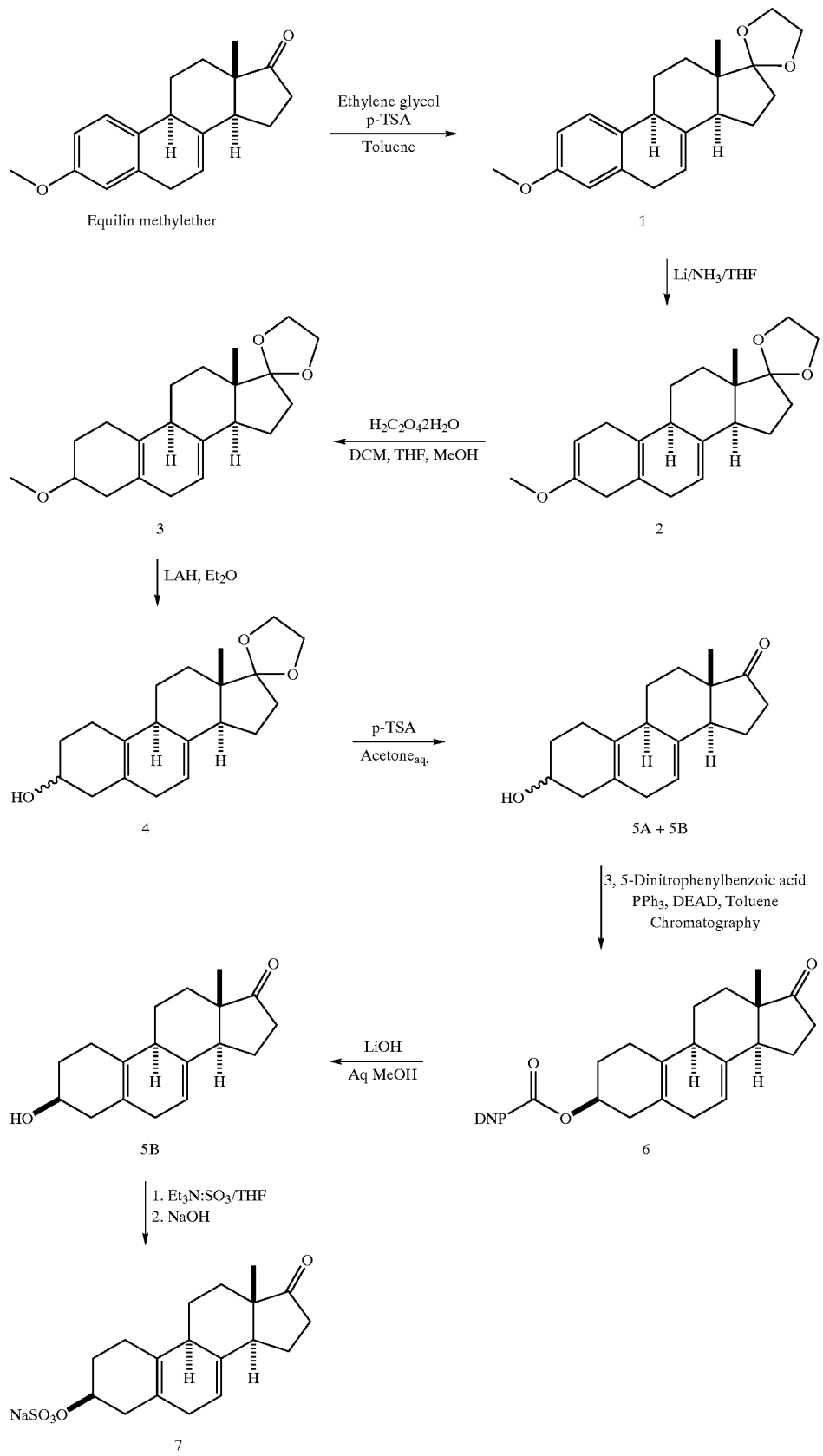

Scheme II outlines the conversion of 17β-hydroxyestra-5(10),7-dien-3-one (8) to a mixture of 5A and 5B (6.6:1 ratio) by a reduction-oxidation sequence requiring a differential protection-deprotection sequence for the C-3 and C-17 functionalities. Reduction at C-3 utilized lithium tri-tertbutoxyaluminum hydride, a Swern-type oxidation provided the C-17 ketone. Separation of 5A and 5B was achieved by HPLC. The conversion of 5A to the 3α-sulfate 15 with pyridine:sufur trioxide reagent is exemplified. The alkali metal salts of 5A and 5B can be prepared by treatment of the respective alcohol with an alkali metal hydride, such as sodium hydride, in a non-aqueous solvent such as THF or DMF. The alkali metal salts of 5A and 5B are useful as intermediates in the preparation of the sulfate esters (via amine:sulfur trioxide treatment) of 5A and 5B, and are also useful as estrogenic compounds.

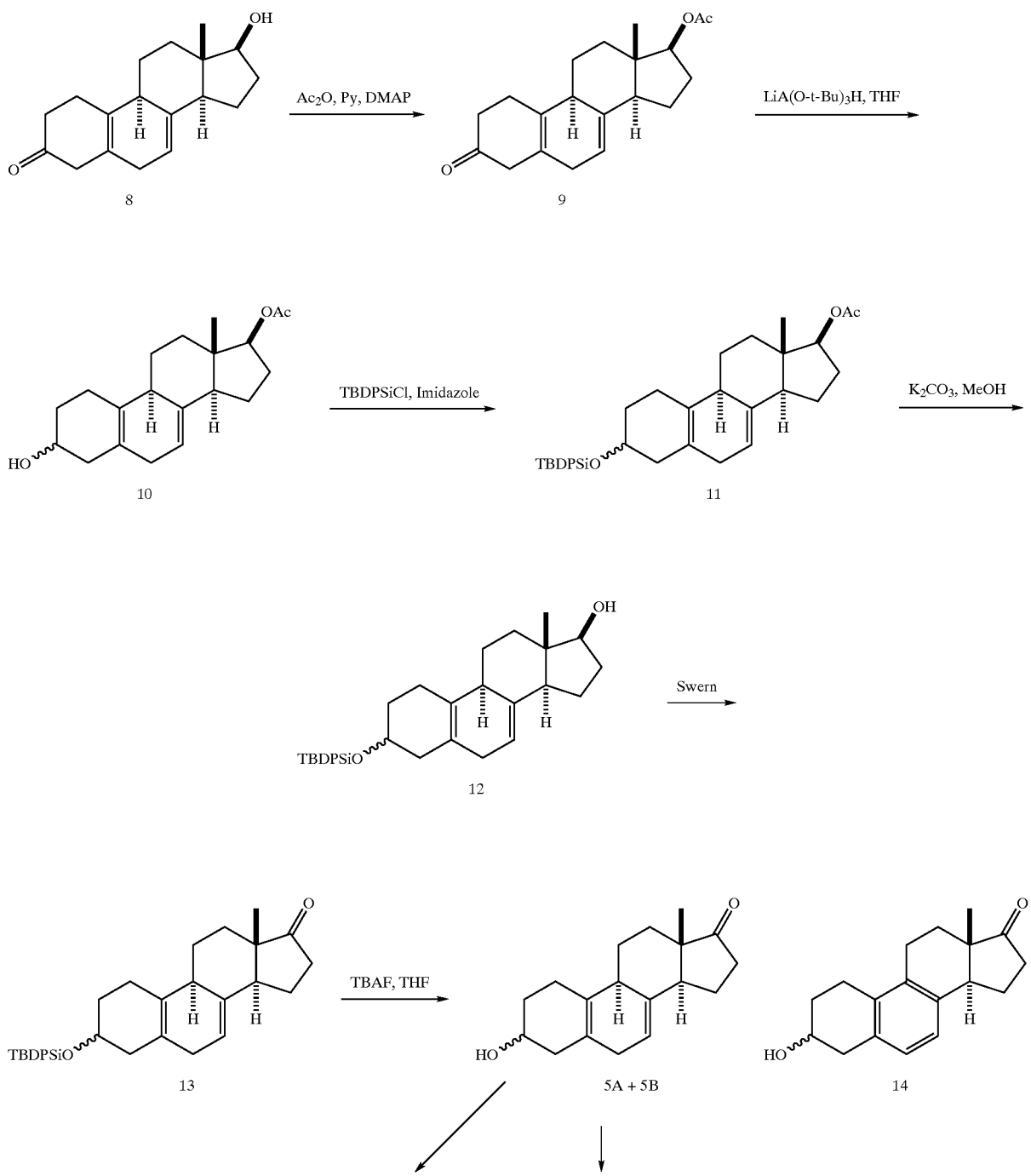

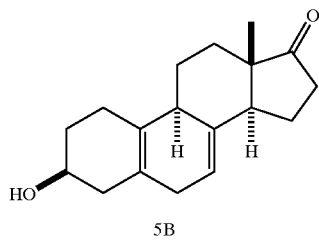

5B

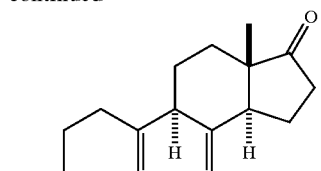

5A i py:SO₃, THF
ii Dowex Na resin
iii chromatography/TEAA

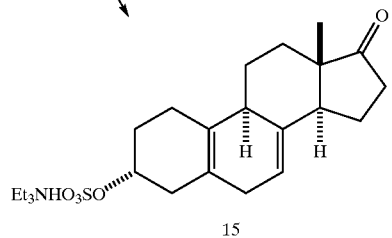

15

Scheme III shows the preparation of estra-5(10),7-dien-3β-ol-17-one 3-glucuronide sodium salt (16) and estra-5(10),7-dien-3α-ol-17-one 3-glucuronide sodium salt (17) from estra-5(10),7-dien-3β-ol-17-one (5B) and estra-5(10),7-dien-3α-ol-17-one (5A), respectively. The sodium glucuronides (16) and (17) can be treated with mild acid to provide the respective 3-glucuronides.

Scheme III

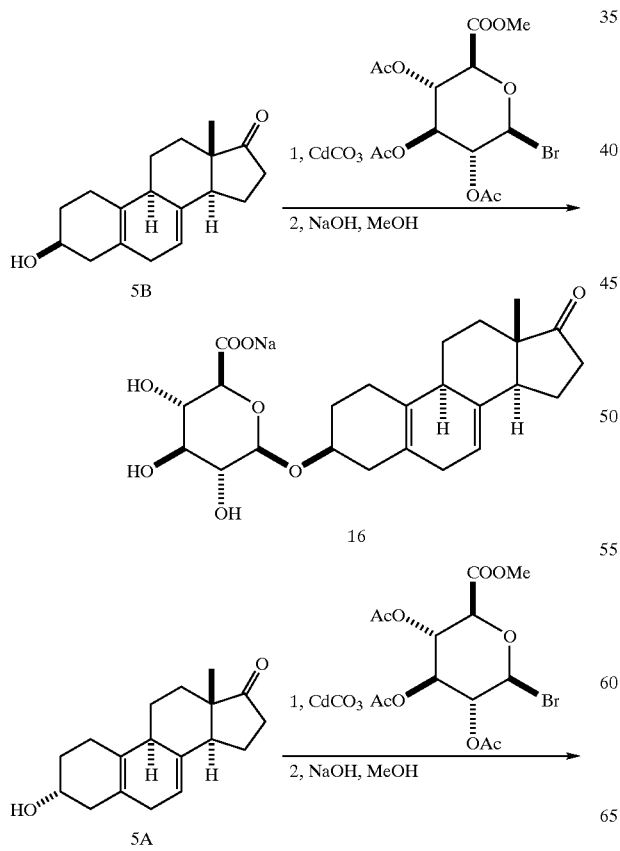

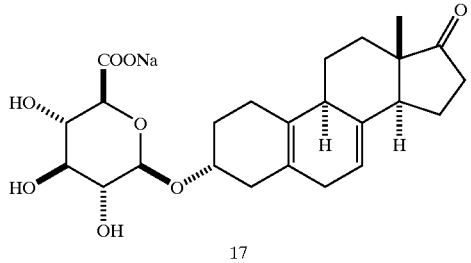

17

The compounds of this invention are estrogenic, as shown in the in vitro and in vivo standard pharmacological test procedures described below in which compounds estra-5(10),7-dien-3β-ol-17-one (5B) and estra-5(10),7-dien-3α-ol-17-one (5A) were evaluated as representative compounds of this invention.

Estrogen Receptor Binding

An initial evaluation examined the competitive binding properties of 5B and 5A to the human estrogen receptor (hER-α) prepared as a soluble cell extract (cytosol). In this standard pharmacological test procedure, 5B and 5A demonstrated no specific binding activity. However, when estrogen receptor binding was analyzed using a whole cell test procedure, specific binding was clearly demonstrated. This test procedure indicated an $IC_{50}$ of $1.5 \times 10^{-7}$ M or an estimated $K_i$ of 150 nM for 5B. Similarly, 5A demonstrated an $IC_{50}$ of $2 \times 10^{-7}$ M. This would be compared with a $K_i$ for estrone, equilin and equilenen of 51, 67 and 375 nM, respectively.

In Vitro Co-Transfection Test Procedure

In this standard pharmacological test procedure, hER-α over-expressed in Chinese hamster ovary (CHO) cells infected with adeno-2x-ERE-tk-luciferase, an estrogen responsive reporter gene construct, cells were exposed to varying concentrations ($10^{-12}$–$10^{-5}$M) of 5B or 5A for 24 hours. Cells were also exposed to 17β-estradiol at $10^{-9}$ M. Following the 24-hour treatment, cells were lysed and cell extracts assayed for luciferase activity. The results provided that 5B had an $EC_{50}$ of approximately 29 nM and 5A of 43 nM. Using a similar test procedure, previous data indicate a 5.6 nM $EC_{50}$ for estrone.

In Vivo Uterotropic Activity

Immature rats were treated with varying doses of 5B or 5A for three days (S.C.) as well as additional groups (n=6) of rats treated with 0.5 μg ethinyl estradiol and vehicle as positive and negative controls, respectively. The results of this standard pharmacological test procedure are presented in the table below.

| Treatment (n = 6/group) | Uterine Weight (mg) ± SD | Significant Differences from Vehicle |
| --- | --- | --- |
| Vehicle | 25.4 ± 4.4 | — |
| Ethinyl Estradiol (0.5 μg) | 101.2 ± 2.8 | p < .001 |
| 5B (500 μg) | 82.6 ± 8.6 | p < .001 |
| 5B (100 μg) | 79.7 ± 5.8 | p < .001 |
| 5B (10 μg) | 43.5 ± 6.9 | p < .001 |
| 5B (1 μg) | 31.7 ± 6.6 | p = .11 |
| 5B (0.1 μg) | 34.1 ± 6.2 | p = .03 |
| 5A (500 μg) | 78.9 ± 13.6 | p < .001 |
| 5A (100 μg) | 66.5 ± 4.7 | p < .001 |
| 5A (10 μg) | 33.3 ± 4.4 | p = .048 |
| 5A (1 μg) | 28.7 ± 2.7 | p = .40 |

The results obtained demonstrate significant uterine stimulation compared with vehicle at almost all doses. At doses above 10 μg/rat, the difference from vehicle was significant at a p-value less than 0.001 for both 5B and 5A. The estimated $EC_{50}$ from this test procedure would be approximately 30 μg/rat or 0.6 mg/kg for 5B and somewhat lower for 5A. The $EC_{50}$ for estrone has been estimated to be 0.2 mg/kg in similar test procedures. Thus, the data from this in vivo standard pharmacological test procedure data demonstrate that 5B and 5A have significant estrogenic activity.

Based on the results of these standard pharmacological test procedures using representative compounds of this invention, estra-5(10),7-dien-3β-ol-17-one or a pharmaceutically acceptable salt of its 3-sulfate ester, estra-5(10),7-dien-3β-ol-17-one 3-glucuronide or a pharmaceutically acceptable salt thereof, estra-5(10),7-dien-3α-ol-17-one or a pharmaceutically acceptable salt of its 3-sulfate ester, estra-5(10),7-dien-3α-ol-17-one 3-glucuronide or a pharmaceutically acceptable salt thereof, estra-5(10),7-dien-3β-ol-17-one 3-alkali metal salt, and estra-5(10),7-dien-3α-ol-17-one 3-alkali metal salt are useful in replacement therapy in estrogen deficiency. The compounds of this invention are therefore useful in providing estrogen replacement therapy following ovariectomy or menopause, and in relieving symptoms related to estrogen deficiency, including vasomotor symptoms, such as hot flushes, and other menopausal related conditions, such as vaginal atrophy, vaginitis, and atrophic changes of the lower urinary tract which may cause increased urinary frequency, incontinence, and dysuria. The compounds of this invention are useful in preventing bone loss and in the inhibition or treatment of osteoporosis. The compounds of this invention are cardioprotective and they are useful in the treatment of atherosclerosis. These cardiovascular protective properties are of great importance when treating postmenopausal patients with estrogens to prevent osteoporosis and in the male when estrogen therapy is indicated. The compounds of this invention are also antioxidants, and are therefore useful in treating or inhibiting free radical induced disease states. Specific situations in which antioxidant therapy is indicated to be warranted are with cancers, central nervous system disorders, Alzheimer's disease, bone disease, aging, inflammatory disorders, peripheral vascular disease, rheumatoid arthritis, autoimmune diseases, respiratory distress, emphysema, prevention of reperfusion injury, viral hepatitis, chronic active hepatitis, tuberculosis, psoriasis, systemic lupus erythematosus, adult respiratory distress syndrome, central nervous system trauma and stroke. Additionally, the compounds of this invention are useful in the suppression of lactation, and in the prophylaxis and treatment of mumps orchitis.

The compounds of this invention can be used alone as a sole therapeutic agent or can be used in combination with other agents, such as other estrogens, progestins, or and androgens.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.02 $\mu$g/kg–750 $\mu$g/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following provides the preparation of representative compounds of this invention. In particular the preparation of the compounds shown in Schemes I and II are described. The compound numbering used in these schemes is also used in the following examples.

EXAMPLE 1

Preparation of:

Estra-5(10),7-dien-3$\beta$ol-17-one (5B)

Estra-5(10),7-dien-3$\beta$ol-17-one 3-sulfate ester sodium salt (7)

17-Ethylenedioxy-3-methoxyestra-1.3.5(10),7-tetraene (1)

A suspension of equilin 3-methylether (5 g, 18 mmol), ethylene glycol (10 mL, 0.18 mol) and p-toluenesulfonic acid monohydrate (0.1 g, 0.53 mmol) in toluene (100 mL) was heated to reflux for 8 h with azeotropic removal of water using a Dean-Stark apparatus. The reaction mixture was washed with 5% aqueous potassium bicarbonate (2×25 mL). The organic layer was separated, dried over anhydrous potassium carbonate and concentrated to give 1 as a white solid (5.8 g, 99%).

$^1$H NMR (CDCl$_3$) 7.8–6.74 (m, 3H), 5.4 (br s, 1H), 3.88 (m, 4H), 3.74 (s, 3H), 0.75 (s, 3H)

$^{13}$C NMR (CDCl$_3$) 157.94, 134.84, 130.72, 129.48, 119.94, 114.70, 113.13, 112.83, 65.82, 65.14, 55.56, 50.25, 48.32, 40.72, 34.86, 32.80, 32.56, 30.48, 14.63

17-Ethylenedioxy-3-methoxyestra-2,5(10),7-triene (2)

To a solution of the arene 1 (1.63 g, 5 mmol) in THF (25 mL) was condensed liquid ammonia (100 mL). Small pieces of freshly cut lithium wire (0.6 g, 86 mmol) were added over a period of 5 min at −50° C. The deep blue solution was stirred at −33° C. for 30 min and ethanol (100%, 10 mL) was added over a period of 10 min. The ammonia was allowed to evaporate and water (20 mL) was added. The biphasic mixture was transferred to a separatory funnel and extracted with ether (3×30 mL). The ether extracts were combined, washed with brine, dried over potassium carbonate and concentrated to afford a shiny white solid which was washed with ether (4×20 mL) to give the enol ether 2 (1.2 g, 73%).

$^1$H NMR (CDCl$_3$) 5.27 (br s, 1H), 4.66 (br s, 1H), 3.91 (m, 4H), 3.56 (s, 3H), 0.74 (s, 3H)

$^{13}$C NMR (CDCl$_3$) 152.86, 137.94, 126.96, 123.11, 119.97, 114.76, 90.98, 65.64, 65.04, 54.20, 49.90, 48.42, 42.50, 34.74, 33.68, 31.72, 29.31, 28.91, 20.45, 14.83

17-Ethylenedioxyestra-5(10),7-dien-3-one (3)

To a solution of the enol ether 2 (0.5 g, 1.52 mmol) in dichloromethane (30 mL), THF (20 mL) and methanol (20 mL) was added water (30 mL) followed by oxalic acid dihydrate (1.2 g, 9.5 mmol) and the resulting biphasic mixture was vigorously stirred for 8.5 h. The layers were separated and the aqueous layer washed with dichloromethane (2×20 mL). The organic layers were combined, dried over anhydrous potassium carbonate and concentrated to give the ketone 3 as a glassy solid (0.47 g, 98%).

$^1$H NMR (CDCl$_3$) 5.27 (br s, 1H), 3.89 (m, 4H), 0.73 (s, 3H)

$^{13}$C NMR (CDCl$_3$) 212.21, 137.85, 129.95, 123.85, 119.76, 114.33, 65.61, 64.99, 49.72, 48.19, 44.10, 43.40, 39.56, 34.67, 31.86, 31.73, 29.26, 28.87, 20.34, 14.81

17-Ethylenedioxyestra-5(10),7-dien-3-ol (4)

To a well-stirred suspension of lithium aluminum hydride (0.3 g, 7.9 mmol) in diethyl ether (20 mL) at 0° C. under nitrogen was added a solution of the ketone 3 (0.47 g, 1.52 mmol) in ether (20 mL). After stirring for 1.5 h the reaction mixture was quenched by the sequential addition of water (0.3 mL), 15% aqueous sodium hydroxide (0.3 mL) and water (1 mL) and stirred for 30 min. The inorganic precipitate was filtered out and washed with ether (3×10 mL). The ether extracts and washings were combined and concentrated to afford a mixture (4:1) of the 3$\alpha$-and 3$\beta$-alcohols 4 as a foam (0.47 g, quant).

$^1$H NMR (CDCl$_3$) 5.17 (br s, 1H), 3.98 (m, 0.2H), 3.88 (m, 0.8H), 3.8 (m, 4H), 0.66 (s, 0.6H), 0.65 (s, 2.4H)

3$\alpha$-Hydroxyestra-5(10),7-dien-17-one (5A) and 3$\beta$-Hydroxyestra-5(10),7-dien-17-one (5B)

To a solution the alcohols 4 (0.46 g, 1.45 mmol) in acetone (10 mL), THF (3 mL) and water (1 mL) was added p-toluene sulfonic acid monohydrate (0.1 g, 0.52 mmol). After stirring for 10 h the reaction mixture was diluted with ether (50 mL) and washed with aqueous 5% potassium bicarbonate (2×20 mL), brine (25 mL) and dried over anhydrous sodium sulfate. Concentration of the organic layer gave a mixture of the alcohols 5A and 5B as a waxy solid (0.45 g, quant).

HPLC (IB-SIL C18-BD, 8 $\mu$, 50×250 mm, 60% methanol in water, 205 nm) separation of 0.35 g of an $\alpha/\beta$ mixture of alcohols provided 5A (0.145 g) and 5B (0.081 g) in pure form.

5A $^1$H NMR (CDCl$_3$) 5.30 (br s, 1H), 3.86 (m, 1H), 0.69 (s, 3H)

$^{13}$C NMR (CDCl$_3$) 220.56, 136.33, 128.45, 123.89, 116.34, 68.07, 50.68, 50.12, 43.47, 39.64, 36.18, 32.58, 32.33, 32.27, 28.41, 27.66, 20.03, 14.14

5B $^1$H NMR (CDCl$_3$) 5.38 (br s, 1H), 4.08 (m, 1H), 0.76 (s, 3H)

$^{13}$C NMR (CDCl$_3$) 220.56, 136.35, 128.40, 122.99, 116.41, 66.59, 50.75, 50.12, 43.24, 38.84, 36.17, 32.41, 32.38, 30.80, 28.39, 24.32, 20.00, 14.14

3β-(3,5-Dinitrobenzoyloxy)estra-5(10),7-dien-17-one (6)

To a suspension of the alcohols 5 (0.45 g, 1.6 mmol), 3,5-dinitrobenzoic acid (0.44 g, 2 mmol) and triphenylphosphine (0.52 g, 2 mmol) in toluene (20 mL) at 0° C., under nitrogen, was added diethylazodicarboxylate (0.32 mL, 2 mmol) dropwise over a period of 2 min. The reaction mixture was allowed to warm to room temperature and stirred for 16 h. It was then heated to 55–58° C. for 4 h and concentrated to dryness. The crude product was purified by flash chromatography, eluting with hexanes/ethyl acetate (7:3) to give the ester 6 as a yellow solid (0.13 g, 17.4%).

$^1$H NMR (CDCl$_3$) 9.2–8.4 (m, 3H), 5.54 (m, 1H), 5.41 (br s, 1H), 0.80 (s, 3H)

3β-Hydroxyestra-5(10),7-dien-17-one (5B)

A solution of the ester 6 (0.13 g, 0.28 mmol) in THF (10 ML) and water (2 mL) was treated with potassium carbonate (0.02 g, 0.14 mmol) and stirred for 8 h. Lithium hydroxide (0.02 g, 0.84 mmol) was added and stirring was continued an additional 30 min. The reaction mixture was diluted with ether (20 mL), washed with aqueous 5% potassium bicarbonate (2×20 mL) and dried over anhydrous sodium sulfate. Evaporation of solvents gave the alcohol 7 as a waxy solid (0.073 g, 96%) with a purple hue. This product was found to be contaminated with small amounts of 3β-hydroxyestra-5(10),6,8-trien-17-one 14.

$^1$H NMR (CDCl$_3$) agrees with the sample obtained from the preparative HPLC separation of 5A and 5B.

GC/MS (silylated derivative) Analysis of 5B: M/Z=344; retention time 15.592 min.

3β-Hydroxyestra-5(10),7-dien-17-one, 3-sulfate ester sodium salt (7)

Crude alcohol 5B (0.07 g, 0.25 mmol) was dissolved in THF (5 mL) and treated with triethylamine-sulfur trioxide complex (0.1 g, 0.55 mmol) for 48 h. The crystalline precipitate was isolated through filtration, dissolved in water (5 mL) and treated with 0.1 NaOH$_{aq}$. to pH 10. The aqueous solution was washed with ether (2×10 mL) and lyophilized to provide 7 as a fluffy solid (70 mg).

LC/MS (Negative Ion Electron Spray) Analysis of 7: M/Z=351; retention time=31.54 mins.

$^1$H NMR (CDCl$_3$) 0.78 (1H), 1.30 (1H), 1.47 (td, 1H), 1.77 (1H), 1.80 (1H), 1.84 (1H), 1.88 (1H), 1.93 (1H), 2.02 (1H), 2.08 (1H), 2.19 (dd, 1H), 2.21 (1H), 2.27 (1H), 2.30 (1H), 2.40 (1H), 2.44 (1H), 2.48 (dd, 1H), 2.54 (bd, 1H), 2.63 (bd, 1H), 4.78 (m, 1H), 5.40 (bs, 1H).

$^{13}$C NMR (CDCl$_3$) 14.2, 20.7, 25.0, 29.1, 29.2, 32.8, 33.2, 36.7, 36.9, 44.2, 51.0, 51.5, 75.3, 117.1, 123.6, 129.3, 137.3, 223.3.

EXAMPLE 2

Preparation of:

Estra-5(10),7-dien-3β-ol-17-one (5B)

Estra-5(10),7-dien-3α-ol-17-one (5A)

Estra-5(10),7-dien-3α-ol-17-one 3-sulfate ester triethylammonium salt (15)

17β-Acetoxyestra-5(10),7-dien-3-one (9)

A solution of 17β-hydroxyestra-5(10), 7-dien-3-one (1.24 g, 4.5 mmol) in a mixture of pyridine (20 mL) and dichloromethane (20 mL) was treated with acetic anhydride (2.0 eq, 0.86 mL) and DMAP (0.1 eq, 10 mg, 0.08 mmol). The solution was stirred 16 h at room temperature and then poured into water (50 mL). The layers were separated and the aqueous layer was extracted with ethyl acetate (3×50 mL). The organic layers were combined, washed with saturated aqueous NaCl solution (50 mL), dried over magnesium sulfate and concentrated under reduced pressure to give an oil that was purified by flash column chromatography on silica gel eluting with 20% EtOAc/hexane to give the acetate (1.03 g, 72%) as a white foam. A small portion was recrystallized from 10% Et$_2$O/hexane to afford white needles (mp 113–4° C.).

$^1$H NMR (400 MHz, CDCl$_3$) δ5.29 (1H, m), 4.77 (dd, J=6.15, 3.7 Hz, 1H), 2.76 (m, 2H), 2.62 (m, 2H), 2.50 (m, 4H), 2.28 (m, 2H), 2.40 (s, 3H), 1.96 (m, 2H), 1.90 (m, 1H), 1.74 (m, 1H) 1.42 (dt, 13.2, 3.9 Hz, 1H), 1.24 (dq, J=12, 3.9 Hz, 1H), 0.69 (s, 3H), m/z (EI) 314 (M$^+$).

Anal. (C$_{20}$H$_{26}$O$_3$) C, H, N: calcd C: 76.4; H, 8.34, N, 0.0; found C, 76.18; H, 8.20; N, 0.06.

17β-Acetoxyestra-5(10),7-dien-3-ol (10)

A solution of the ketone 9 (1.03 g, 3.28 mmol) in dry THF (20 mL) at 0° C. under nitrogen was treated, via syringe, with lithium tri-tert-butoxyaluminohydride (1.0 M, 1.5 eq, 4.92 mL, 4.92 mmol). After 2 h the solution was poured into 1N HCl (100 mL). The layers were separated and the aqueous layer was extracted with ether (3×50 mL). The organic layers were combined, washed with saturated aqueous NaCl solution (50 mL), dried over magnesium sulfate and concentrated under reduced pressure to give a white solid (1.08 g), R$_f$0.3 (30% EtOAc/hexane), which was used without further purification.

17β-Acetoxy-3-(tert-butyldiphenylsilyl)oxyestra-5(10),7-diene (11)

To a solution of the alcohols 10 (1.08 g, 3.42 mmol) in dichloromethane (20 mL) was added imidazole (1.6 eq, 0.37 g, 5.43 mmol) followed by tert-butyldiphenylsilylchloride (1.6 eq, 1.42 mL, 3.64 mmol). The mixture was stirred 16 h at room temperature under nitrogen then poured into 1N HCl (100 mL). The layers were separated and the aqueous layer was extracted with ether (3×50 mL). The organic layers were combined, washed with saturated aqueous NaCl solution (50 mL), dried over magnesium sulfate and concentrated under reduced pressure to give an oil (2.2 g), R$_f$ 0.55 (10% EtOAc/hexane), which was used without further purification.

3-(tert-Butyldiphenylsilyl)oxy-17β-hydroxyestra-5(10),7-diene (12)

To the acetates 11 (2.2 g, 4.0 mmol) in a mixture of methanol (60 mL) and dichloromethane (10 mL) was added potassium carbonate (0.1 eq, 55 mg, 0.4 mmol). After stirring for 4 h an additional portion of potassium carbonate (1.0 eq, 0.55 g, 4.0 mmol) was added. The mixture was stirred 16 h and more potassium carbonate (1.0 eq, 0.55 g, 4.0 mmol) was added. After 24 h water (100 mL) was added, the layers were separated and the aqueous layer was extracted with dichloromethane (3×100 mL). The organic layers were combined, washed with saturated aqueous NaCl solution (100 mL), dried over magnesium sulfate and concentrated under reduced pressure to give an oil that was purified by flash column chromatography on silica gel eluting with 20% EtOAc/hexane to give the alcohols 12 (1.34 g), R$_f$0.5 (30% EtOAc/hexane), as a white foam which was used directly.

3-(tert-Butyldiphenylsilyl)oxyestra-5(10),7-dien-17-one (13)

To the alcohols 12 (1.34 g, 2.6 mmol) in DMSO (20 mL) containing triethylamine (11 eq, 4.0 mL, 28.7 mmol) was added trimethylamine-sulfur trioxide complex (5.4 eq, 1.97 g, 14 mmol). After stirring for 16 h under nitrogen water (100 mL) was added to the mixture and the aqueous phase was extracted with Et$_2$O (6×100 mL). The organic layers were combined and washed successively with 1N aqueous HCl (100 mL), saturated aqueous sodium bicarbonate solution (100 mL) and saturated aqueous NaCl solution (100 mL). The organic layer was dried over magnesium sulfate and concentrated under reduced pressure to give an oil that was purified by flash column chromatography on silica gel eluting with 10% EtOAc/hexane to give the silyl protected alcohols 13 (1.34 g), R$_f$0.5 (20% EtOAc/hexane), as a white foam which was used directly.

Estra-5(10),7-dien-3α-ol-17-one (5A) and Estra-5(10),7-dien-3β-ol-17(5B)

To a solution of the silyl protected alcohols 13 (1.16 g, 2.3 mmol) in THF (10 mL) at room temperature under nitrogen was added, via syringe, a solution of tetrabutylammonium fluoride (1.0 M, 1.3 eq, 2.9 mL, 3 mmol). After stirring for 24 h the solution was poured into water (100 mL) and the aqueous layer was extracted with ethyl acetate (3×100 mL). The organic layers were combined and washed successively with 1N aqueous HCl (100 mL), saturated aqueous sodium bicarbonate solution (100 mL) and saturated aqueous NaCl solution (100 mL). The organic layer was dried over magnesium sulfate and concentrated under reduced pressure to give an oil that was purified by flash column chromatography on silica gel, eluting with 40% EtOAc/hexane to provide a white foam (0.56 g). Further purification by preparative HPLC (Primesphere, C$_{18}$—HC, 10μ, 50×20 mm; isocratic: 50/50 MeCN/H$_2$O; Flow 50 mL/min)gave—

14[t$_R$=13.85 min, stereoisomers of the B-ring aromatic analog]

$^1$H NMR (300 MHz, CDCl$_3$) δ6.96 (brs, 2H) 4.15 (m, 1H), 2.97 (m, 2H), 2.95–2.50 (m, 6H), 2.50–2.25 (m, 2H), 2.05 (m, 2H), 1.85 (m, 3H), 0.77 and 0.75 (2 singlets, 2H). m/z (ES-pos) 293 (M+Na$^+$)

5A [t$_R$=17.16 min] (330 mg), mp 139–42° C.
$^1$H NMR (300 MHz, CDCl$_3$) δ5.37 (m, 1H), 3.93 (m, 1H), 2.61 (m, 2H), 2.48 (m, 2H), 2.45–2.10 (m, 5H), 2.10–1.80 (m, 7H), 1.7–1.4 (m, 2H), 1.26 (m, 2H), 0.76 (s, 3H).
m/z (ES-pos) 295 (M+Na$^+$).

5B [t$_R$=18.68 m] (50 mg), mp 124–7° C.
$^1$H NMR (300 MHz, CDCl$_3$) δ5.38 (m, 1H), 4.10 (m, 1H), 2.75–2.45 (m, 3H), 2.45–2.15 (m, 5H), 2.15–1.95 (m, 2H), 1.95–1.70 (m, 7H), 1.65–1.40 (m, 3H), 1.27 (m, 12H), 0.76 (s, 3H). m/z (ES-pos) 295 (M+Na$^+$).

Estra-5(10),7-dien-3α-ol-17-one, 3-sulfate ester triethylammonium salt (15)

To a solution of the alcohol 5A (0.183 g, 0.67 mmol) in THF (2 mL) at room temperature was added pyridine-sulfur trioxide complex (1.3 eq, 0.14 g, 0.87 mmol). The mixture was stirred 4 days under nitrogen and then the THF was removed under reduced pressure. The solid residue was washed with ether (20 mL) and dissolved in a mixture of methanol (10 mL) and water (10 mL). Dowex-50 resin (700 mg) was added, the mixture was concentrated under reduced pressure and transferred to a sintered glass funnel. The resin was washed with methanol/water (1:1) until TLC analysis of the washings indicated all the product (ca. 200 mg) had been washed off. Further purification by HPLC (converted to the product to the triethylammonium salt during chromatography) (Primesphere, C$_{18}$—HC, 10μ, 50×250 mm, S#171320; 10/90 to 25/75 @ 5' to 50/50 @ 15' to 60/40 @ 23' to 65/35 @ 26.5' to 90/10 @ 31' (MeOH/50 mM triethylammonium acetate (TEAA); pH=7); Flow 70.0 mL/min); 950PSI 850UV=214nm; 900PSI gave 15 [t$_R$=31 min] (21 mg, 7%) as a gum.

$^1$H NMR (300 MHz, MeOH-d$_4$)
5.39 (s, 1H), 4.55 (m, 1H), 3.18 (q, J=7.3 Hz, 7.6H), 2.61 (br s, 2H), 2.55–1.60 (m, 16H), 1.50 (m, 1H), 1.30 (t, J=7.3 Hz, 12.5H), 0.76 (s, 3H). m/z (ES-neg) 351 (M−NH(C$_2$H$_5$)$_3^-$).

What is claimed is:

1. A compound which is a pharmaceutically acceptable salt of estra-5(10),7-dien-3β-ol-17-one 3-sulfate ester or estra 5(10),7dien-3β-ol-17-one 3-glucuronide or a pharmaceutically acceptable salt thereof.

2. The compound of claim 1 wherein the pharmaceutically acceptable salt of the 3-sulfate ester or 3-glucuronide is an a metal salt, alkaline earth metal salt, ammonium salt, alkylammonium salt containing 1–6 carbon atoms, or dialkylammonium salt containing 1–6 carbon atoms in each alkyl group, or trialkylammonium salt containing 1–6 carbon atoms in each alkyl group.

3. Estra-5(10),7-dien-3β-ol-17-one 3-sulfate ester sodium salt, which is at least 1 percent pure.

4. A compound which is a pharmaceutically acceptable salt of estra-5(10),7-dien-3α-ol-17-one 3-sulfate ester or estra-5(10),7-dien-3α-ol-17-one 3-glucuronide or a pharmaceutically acceptable salt thereof.

5. The compound of claim 4 wherein the pharmaceutically acceptable salt of the 3-sulfate ester or 3-glucuronide is an alkali metal salt, alkaline earth metal salt, ammonium salt, alkylammonium salt containing 1–6 carbon atoms, or dialkylammonium salt containing 1–6 carbon atoms in each alkyl group, or trialkylammonium salt containing 1–6 carbon atoms in each alkyl group.

6. The compound of claim 4 which is estra-5(10),7-dien-3α-ol-17-one 3-sulfate ester triethylammonium salt.

7. A pharmaceutical composition which comprises estra-5(10),7-dien-3α-ol-17-one or a pharmaceutically acceptable salt of its 3-sulfate ester or estra-5(10),7-dien-3α-ol-17-one 3-glucuronide or a pharmaceutically acceptable salt thereof and a pharmaceutical carrier.

8. A compound which is estra-5(10),7-dien-3β-ol-17-one 3-alkali metal salt.

9. A compound which is estra-5(10),7-dien-3α-ol-17-one 3-alkali metal salt.

* * * * *

UNITED STATES PATENT AND TRADEMARK OFFICE
CERTIFICATE OF CORRECTION

PATENT NO.    : 6,458,778 B1
DATED         : October 1, 2002
INVENTOR(S)   : Kong et al.

It is certified that error appears in the above-identified patent and that said Letters Patent is hereby corrected as shown below:

Column 16,
Line 3, please replace "a metal salt" with -- alkali metal salt --.

Signed and Sealed this

Second Day of December, 2003

JAMES E. ROGAN
*Director of the United States Patent and Trademark Office*